(12) United States Patent
Ledford et al.

(10) Patent No.: US 7,196,233 B2
(45) Date of Patent: Mar. 27, 2007

(54) PROCESS FOR THE PREPARATION OF ALKYLENE GLYCOLS

(75) Inventors: John S. Ledford, Richmond, TX (US); Jaap W. Van Hal, Fresno, TX (US); Xiankuan Zhang, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 217 days.

(21) Appl. No.: 11/005,681

(22) Filed: Dec. 7, 2004

(65) Prior Publication Data

US 2006/0122437 A1    Jun. 8, 2006

(51) Int. Cl.
*C07C 29/10*    (2006.01)

(52) U.S. Cl. ..................................... 568/867

(58) Field of Classification Search ................. 568/867
See application file for complete search history.

*Primary Examiner*—Elvis O. Price
(74) *Attorney, Agent, or Firm*—Jim Wheelington

(57) ABSTRACT

Disclosed is a process for the preparation of alkylene glycols from the corresponding alkylene oxide, such as ethylene glycol from ethylene oxide, in the presence of water, a catalyst and, optionally, carbon dioxide. The catalyst contains an amphoteric compound, such as such as (ethylenedinitrilo) tetraacetic acid (EDTA). These befunctional compounds have both acid and base moieties. Preferably, a compound useful in the present invention forms a buffered solution in water, i.e., the acid and base moieties do not completely disassociate. The pH of the buffered solution should be 2-10, preferably 5-10, more preferably 4-9. A compound useful in the present invention is preferably organic with the base moiety and the acid moiety being separated by one to four carbon atoms.

25 Claims, 11 Drawing Sheets

2-Picolinic acid

D,L-pipecolinic acid

Pipes, Piperazine-1,4-bis(2-ethanesulfonic acid)

Iminodiacetic acid

3-Piperidino-1,2-propanediol

Nitrilotriacetic acid disodium salt

N-Lauroylsarcosine sodium salt (NLS)

SodiumD-isoascorbate monohydrate

Poly-DL-aspartic acid/sodium salt

PROCESS FOR THE PREPARATION OF ALKYLENE GLYCOLS

BACKGROUND OF THE INVENTION

1. Field of the Invention

This invention relates to a process for the preparation of alkylene glycols from the corresponding alkylene oxide in the present of water and an amphoteric catalyst, such as (ethylenedinitrilo)tetraacetic acid (EDTA). A specific example of the process is in the preparation of ethylene glycol from ethylene oxide.

2. Description of the Prior Art

The production of alkylene glycols from alkylene oxides is known and is practiced commercially. Of particular interest is the production of ethylene glycol from ethylene oxide. The thermal hydration of ethylene oxide produces monoethylene glycol (MEG). MEG is mainly used as a base material in the production of polyester fibers, resins, films and bottles and is also a major active component in antifreeze.

Hydration of ethylene oxide can be through catalytic and non-catalytic means. Non-catalytic hydration of ethylene oxide to MEG requires a large excess of water to inhibit the formation of diethylene glycol (DEG) and other higher glycols. Even with a large excess of water the molar selectivity to MEG is only about 90%. In addition, the water must be distilled from the glycol to obtain a high purity product.

While the hydrolysis reaction can proceed uncatalyzed, the presence of acids or bases can enhance the rate of reaction. However, strong acid catalysts and strong base catalysts do have shortcomings. For instance, base catalysts generally do not beneficially affect selectivity to the formation of the monoglycol product and the use of acid catalysts typically is accompanied by corrosion problems. Hence, commercial processes typically utilize relatively neutral hydrolysis conditions (for instance, pH 6-10).

Catalytic hydration of ethylene oxide may use smaller amounts of water and is carried out at lower temperatures than non-catalytic thermal hydration. There are numerous examples of catalysts for hydration of an alkylene oxide to alkylene glycol.

U.S. Pat. No. 6,153,801 discloses preparation of alkylene glycols by reacting an alkylene oxide with water in the presence of a polycarboxylic acid derivative catalyst, preferably immobilized on a solid support. When a strongly basic anion exchange resin is used as the support, amines or phosphines may leach from the resin into the product stream. A guard bed of a strongly acidic ion exchange resin may be used to capture the amines and phosphines. When only the $H^+$ form of the strongly acid resin used as a guard bed, the product stream-may become acidic. Using a mixture of the strongly acidic ion exchange resin in its $H^+$ form and salt form in the guard bed keeps the pH of the product stream close to neutral.

U.S. Pat. No. 5,798,412 discloses a process in which carbon is used to selectively catalyze the hydrolysis of alkylene oxides to monoalkylene glycols. It is disclosed that the hydrolysis reaction may be carried out at any pH but a reactant system typically has a pH of between about 5 and about 10, and most typically between about 6 and about 8.

U.S. Pat. No. 4,967,018 discloses a process for catalytic hydrolysis of an alkylene oxide to an alkylene glycol using catalysts based on anionic clay minerals, such as aluminum and magnesium or nickel hydrotalcite-type or takovite-type materials. In general, the pH of the liquid reaction system is between about 3 and 13, preferably between about 6 and 9.

U.S. Pat. No. 4,937,393 discloses a method of manufacturing ethylene glycol with a catalyst of a carboxylic acid and a carboxylic acid salt or a metal salt of formic acid alone.

U.S. Pat. No. 4,620,044 discloses hydrolysis of olefin oxides to corresponding glycols by a steam stable zeolite in its acid form characterized by a constraint index of about 1 to 12.

U.S. Pat. No. 4,551,566 discloses a process for the liquid phase hydration of alkylene oxides to the corresponding alkylene glycols with a vanadate salt and a pH between about 5 and 12. The particular vanadate species present is thought to be dependent on the pH of the liquid phase. Hence, at a pH of, say, about 12, little, if any, metavanadate anion may exist. Although the processes are carried out by providing a water-soluble vanadate salt to the reaction system, the exact nature of the catalytic species is not fully known.

U.S. Pat. No. 4,393,254 discloses a process for hydrating alkylene oxide in the presence of a partially amine-neutralized sulfonic acid catalyst to produce alkylene glycol.

U.S. Pat. No. 4,277,632 discloses a process for reacting an alkylene oxide with water in the presence of a catalyst having molybdenum and/or tungsten to produce an alkylene glycol. The pH value of the reactant solution need not be specifically limited but may be varied in a wide range such as from 2 to 12. Better results of the reaction are obtained when the pH value is limited to the range of from 5 to 10, desirably from 6 to 8. The hydration of the alkylene oxide produces the best results when it is carried out with the pH value kept in the neutral point of about 7. Any acidic or alkaline substance can be used as an agent for keeping the pH value of the reaction solution in the range of from 5 to 10.

EDTA ((Ethylenedinitrilo)tetraacetic acid, also referred to as ethylenediaminetetraacetic acid) is a known compound. US 2003/0073580 discloses EDTA as a chelate for metals in fertilizer mixtures.

U.S. Pat. No. 6,803,167 discloses salts of EDTA as a surfactant component of a developer in the preparation of lithographic printing plates. A mixture of a salt of EDTA and EDTA is discloses as a buffer system to keep the pH relatively constant.

Amphoteric compounds are known as catalysts. U.S. Pat. No. 4,330,666 discloses a method for making polyetherimides by intercondensation of aromatic bis(ether anhydride) and organic diamine in the presence of an amphoteric catalyst, such as hydroxypyridine.

SUMMARY OF THE INVENTION

This invention is a process for the preparation of alkylene glycols from an alkylene oxide and water in the presence of an amphoteric catalyst, such as (ethylenedinitrilo)tetraacetic acid (EDTA). These amphoteric compounds have both acid and base moieties and are bifunctional. The pH of the compound should be 2-10, preferably 5-10, more preferably 4-9. The catalyst may be a Group 1-12 metal salt derivative. The catalysts may be supported on resins, such as chelating resins which contain an amino-carboxylic acid functional group.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

Alkylene glycols can be obtained by reacting the corresponding alkylene oxide with water in the presence of a catalyst. Carbon dioxide may be added to the reaction medium to improve selectivity to the glycol.

Alkylene oxides are generally of the formula $R^1R^2(COC)R^3R^4$, where each $R^1$, $R^2$, $R^3$ and $R^4$ is independently hydrogen or an alkyl of from 1 to 4 carbon atoms. Examples of alkylene oxides are ethylene oxide, propylene oxide and butylene oxide. The corresponding alkylene glycol is generally of the formula $R^1R^2(COHCOH)R^3R^4$, where $R^1$, $R^2$, $R^3$ and $R^4$ are as defined above, and may be obtained by hydration of the alkylene oxide, i.e., reacting it with water to introduce a hydroxyl group and hydrogenate the oxygen. A mixture of glycols is formed (monoalkylene glycol, dialkylene glycol and higher alkylene glycols).

Though the reaction of alkylene oxide and water to alkylene glycol proceeds non-catalytically, improvements in reaction rate, selectivity and reduced water can be realized by the use of catalysts. The catalysts used in the present invention are amphoteric compounds. These compounds have both acid and base moieties and are bifunctional. The base moiety may be an amine, amide, imide, phosphazene, verkade base, nucleic acid or aminophospholipid group. The acid moiety may be carboxylic, sulfonic, phosphoric, boric, nitric or salts thereof and may contain modifying groups such as nitro, fluorinated alkyl and fluorinated aryl. Preferably, a compound useful in the present invention forms a buffered solution in water, i.e., the acid and base moieties do not completely disassociate. The pH of the buffered solution should be 2-10, preferably 5-10, more preferably 4-9. A compound useful in the present invention is preferably organic with the base moiety and the acid moiety being separated by one to four carbon atoms. The organic compound may be alkyl or aryl or a combination thereof, e.g. arylalkyl or alkylaryl.

Figure 1:
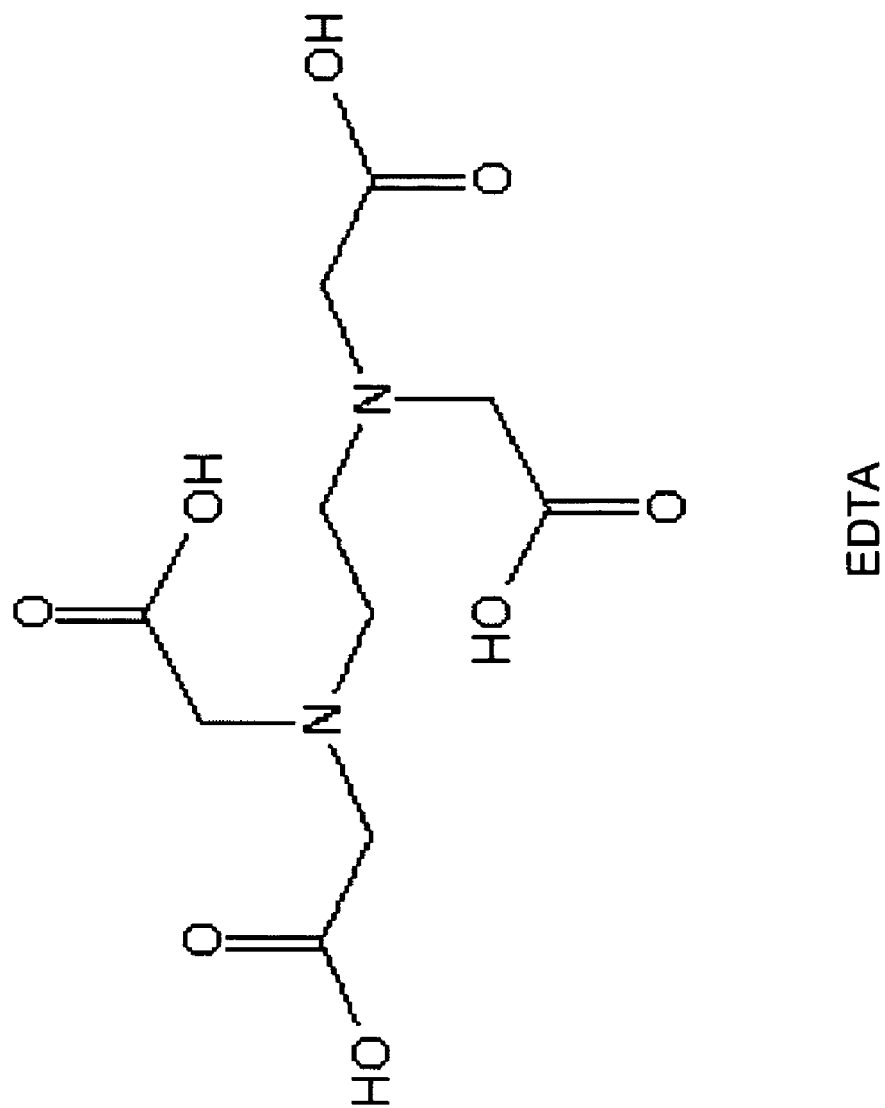
FIG. 1 is a structural representation of ethylenedinitrilo) tetraacetic acid or ethylenediaminetetraacetic acid (EDTA).
Figure 2:
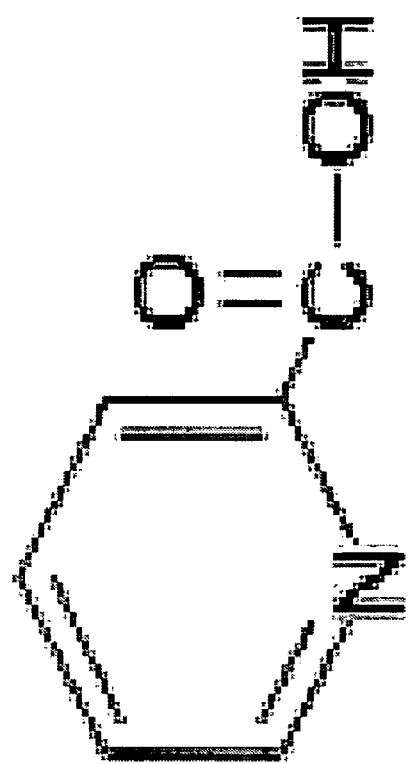
FIG. 2 is a structural representation of 2-picolinic acid.
Figure 3:
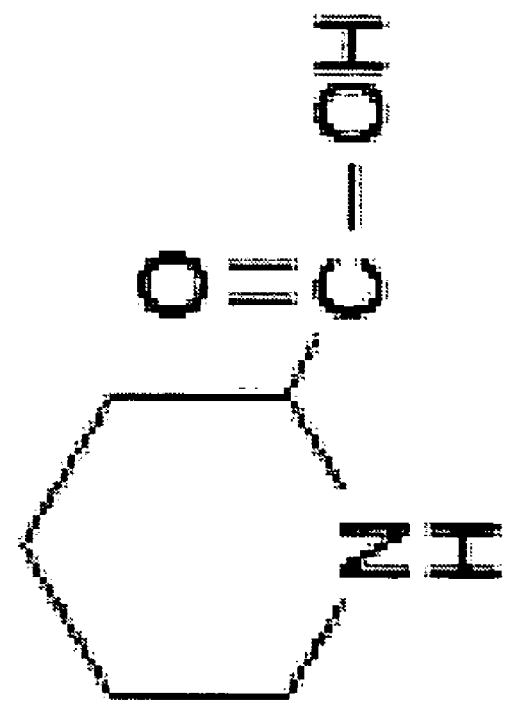
FIG. 3 is a structural representation of D,L-pipecolinic acid.
Figure 4:
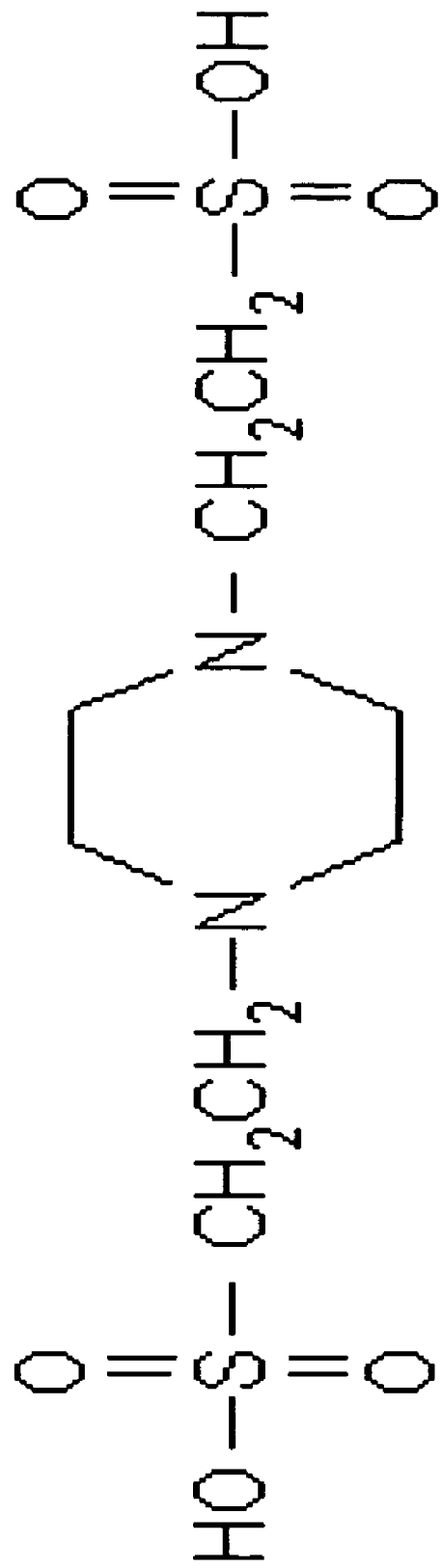
FIG. 4 is a structural representation of piperazine-1,4-bis (2-ethanesulfonic acid) (PIPES).
Figure 5:
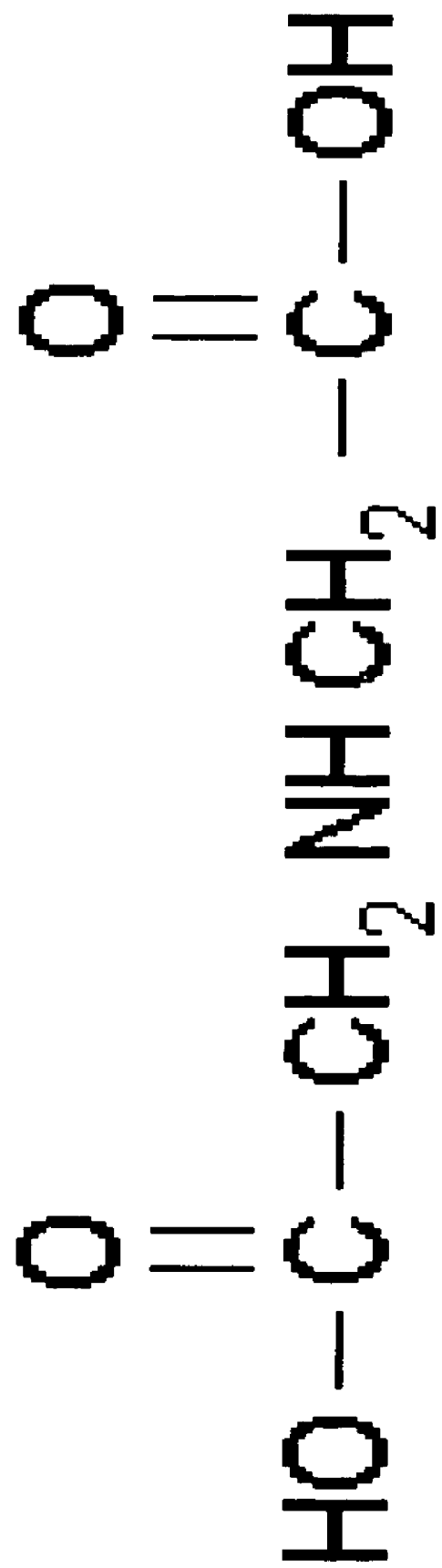
FIG. 5 is a structural representation of iminodiacetic acid.
Figure 6:
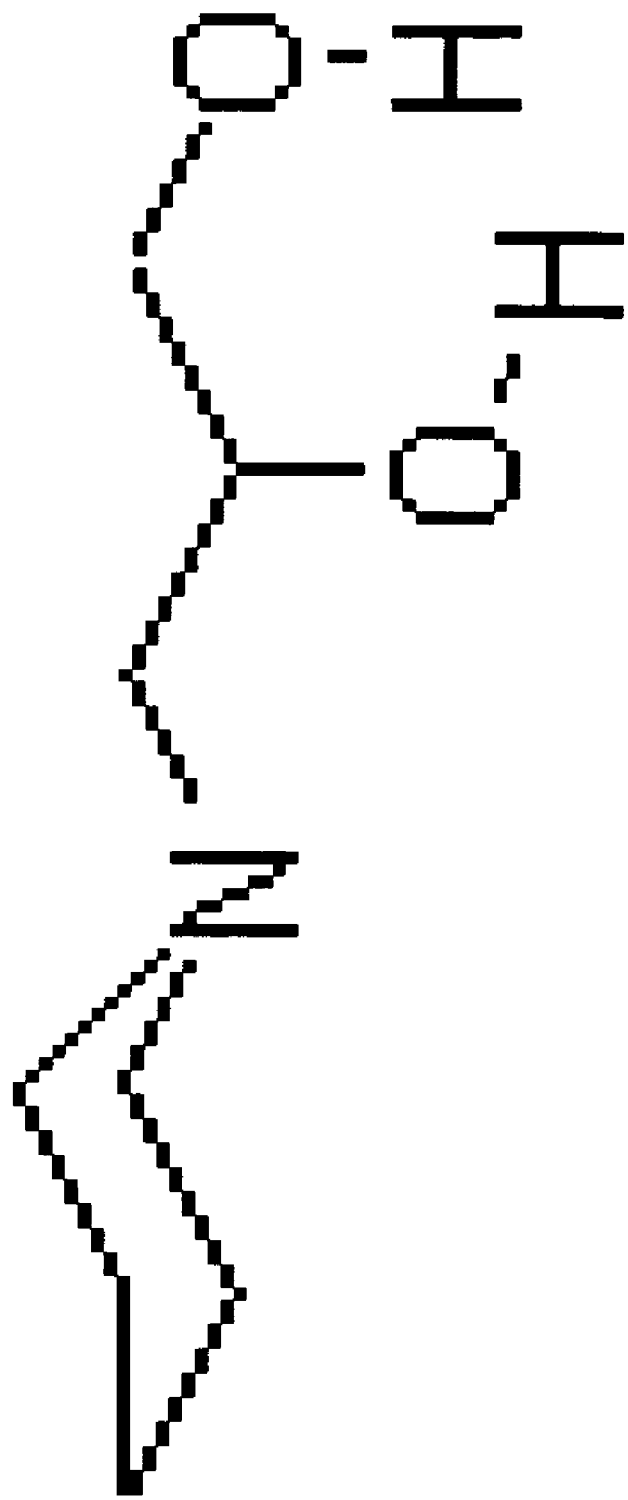
FIG. 6 is a structural representation of 3-piperidino-1,2-propanediol.
Figure 10:
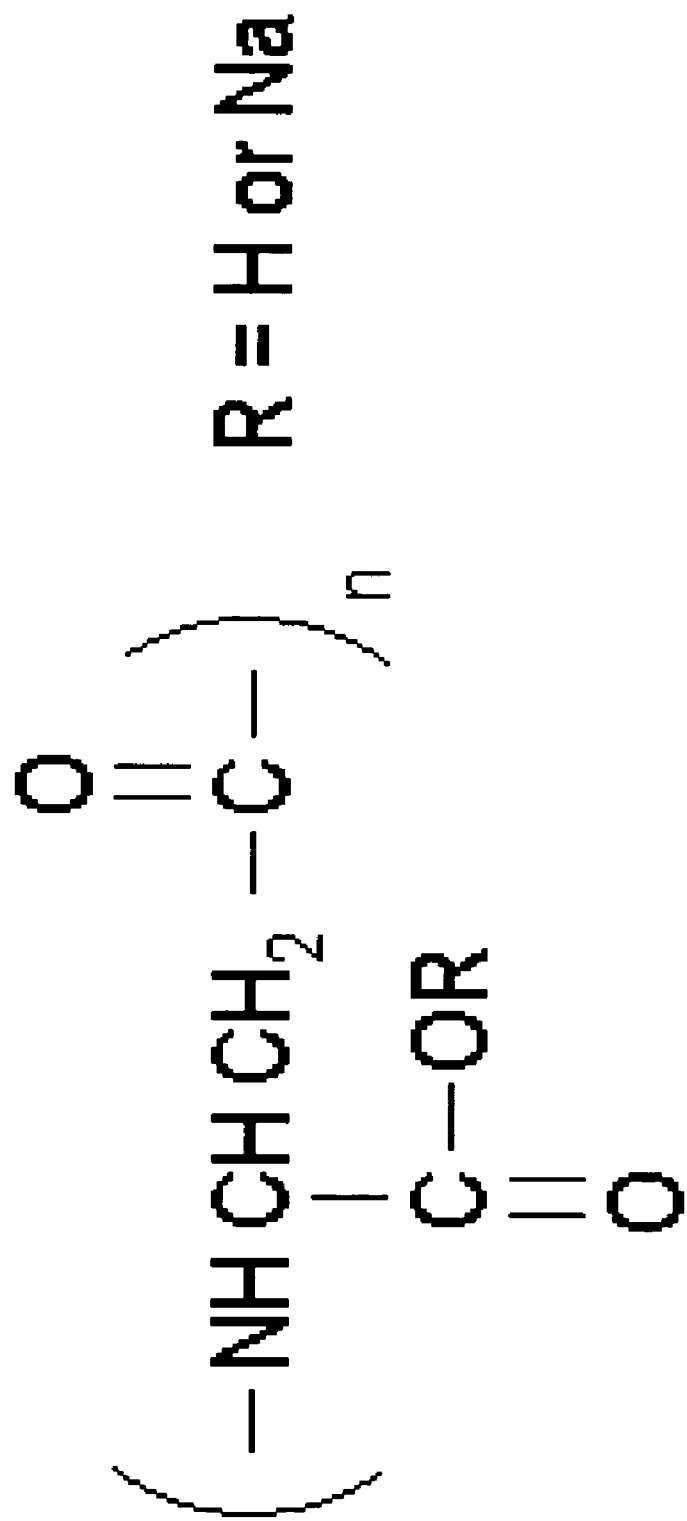
FIG. 10 is a structural representation of poly-D,L-aspartic acid sodium salt.

Examples of compounds useful in the present invention are (ethylenedinitrilo)tetraacetic acid (EDTA, FIG. 1), 2-picolinic acid (FIG. 2), D,L-pipecolinic acid (FIG. 3), piperazine-1,4-bis-(2-ethanesulfonic acid) (PIPES, FIG. 4), imiodiacetic acid (FIG. 5), 3-piperadino-1,2-propanediol (FIG. 6), nitrilotriacetic acid and poly-D-L-aspartic acid (R=H, FIG. 10). In FIGS. 1, 2, 3, 5 and 10 the base moiety (—N—)is separated from the acid moiety (—COOH) by one carbon atom. In FIG. 4 the base moiety (—N—) is separated from the acid moiety (—SOOOH) by two carbon atoms. In FIG. 6 the base moiety is separated from the acid moieties (—COH) by one and three carbon atoms.

Figure 7:
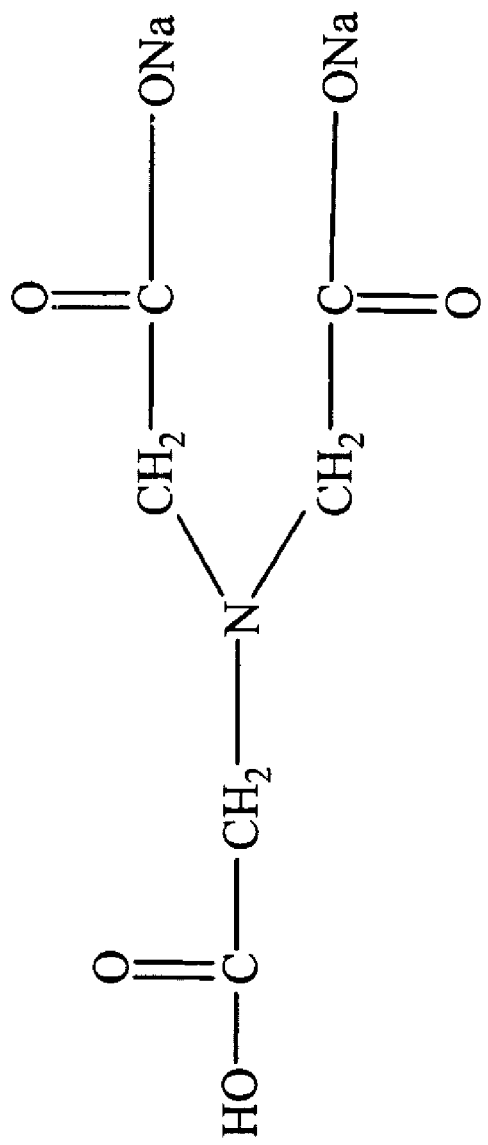
FIG. 7 is a structural representation of nitrolotriacetic acid disodium salt
Figure 8:
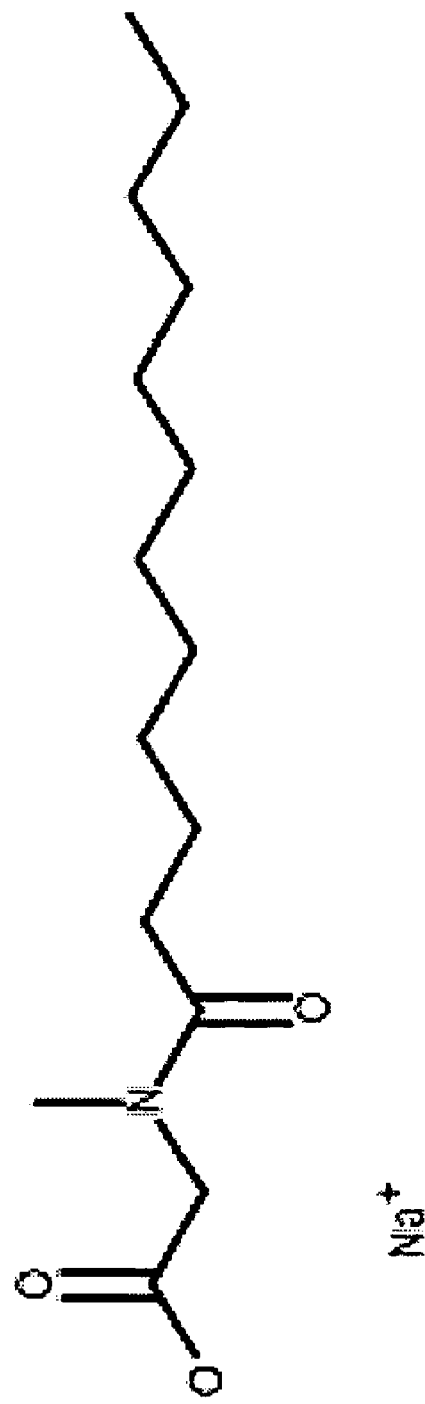
FIG. 8 is a structural representation of N-lauroylsarcosine sodium salt (NLS).
Figure 9:
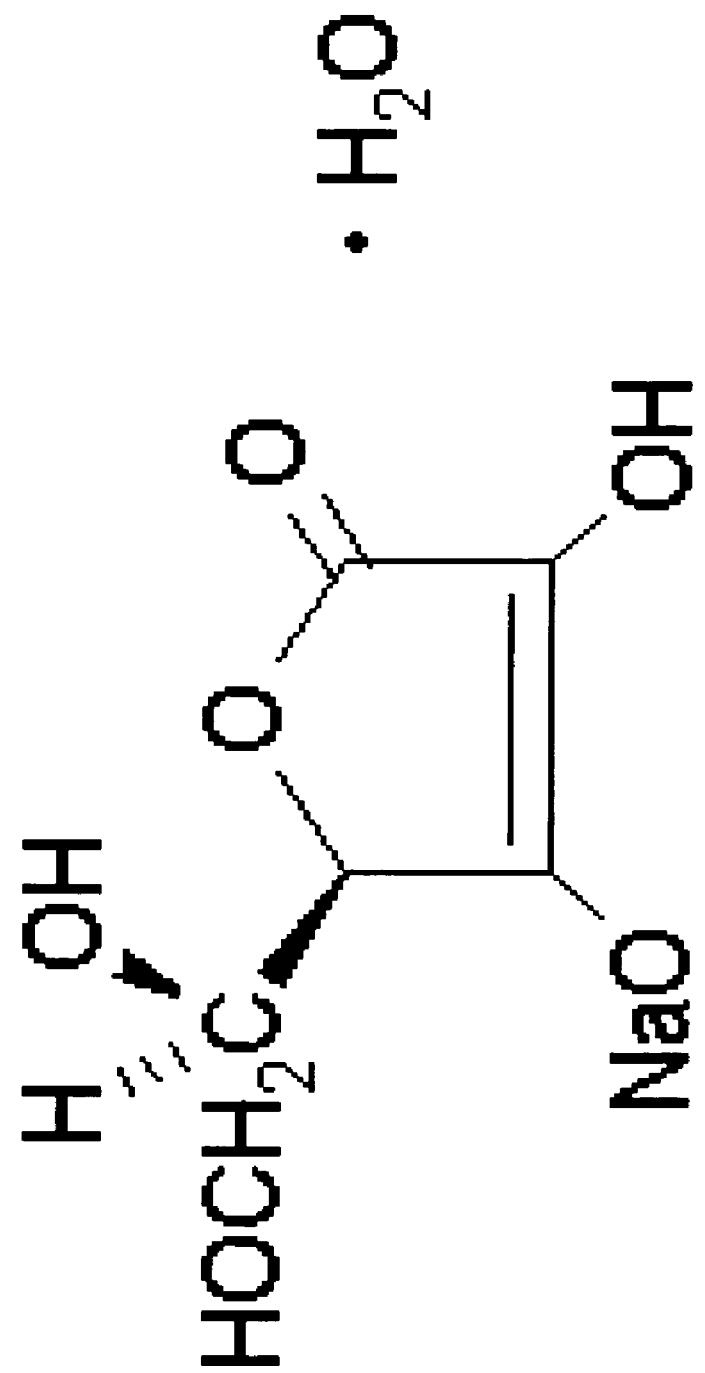
FIG. 9 is a structural representation of sodium-D,L-isoacsorbate monohydrate.

The catalyst may be a Group 1-12 metal salt derivative, preferably a Group 1 metal salt derivative, such as $Na_xEDTA$ or $K_xEDTA$ where x is 1 to 4, preferably 1 to 3 and more preferably 1-2. Other specific examples are imiodiacetic acid disodium salt, piperazine-1,4-bis(2-ethanesulfonic acid) dipotassium salt, nitrilotriacetic acid disodium (FIG. 7), N-lauroylsarcosine sodium salt (NLS, FIG. 8), sodium-D,L-isoascorbate monohydrate (FIG. 9) and poly-D-L-aspartic acid sodium salt (R=Na, FIG. 10). In FIGS. 7, 8 and 10 the base moiety (—N—) is separated from the acid salt moiety (—COONa) by one carbon atom. In FIG. 9, the base moiety (—O—Na) is separated from the acid salt moiety (—C(O)COH) by one carbon atoms.

Figure 11:
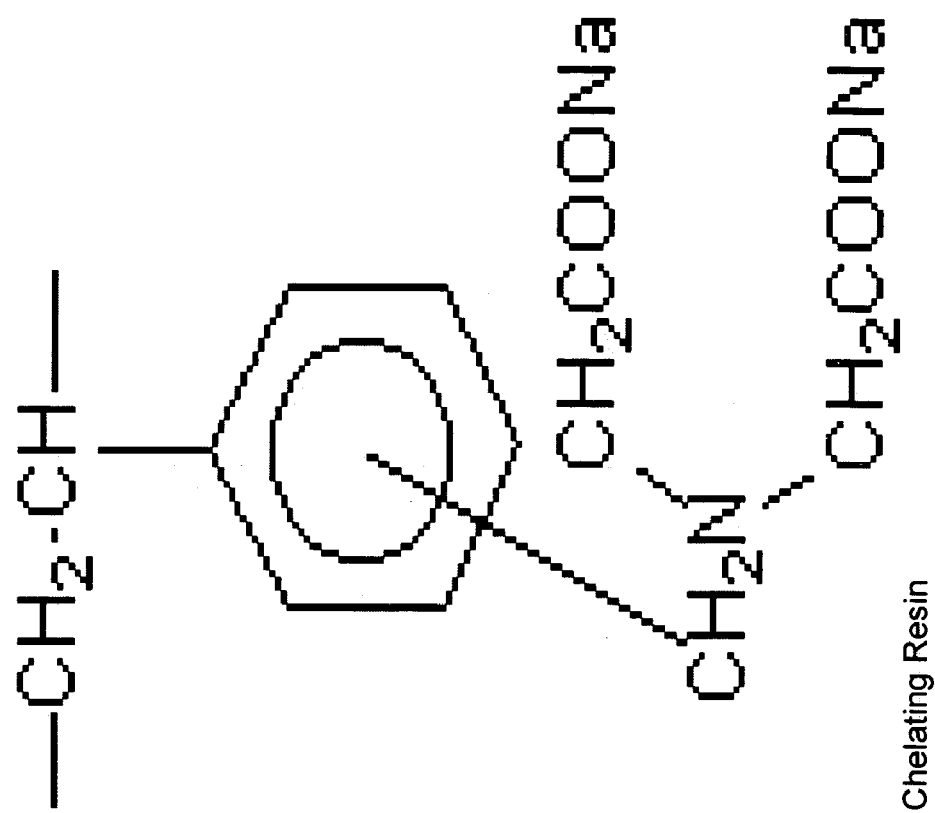
FIG. 11 is a structural representation of a salt form of a chelating resin.

The catalysts used in the present invention may be heterogenized using procedures known in the art. For example, EDTA can be exchanged onto a basic ion exchange resin (IER) and the salts of EDTA could be exchanged onto an acid IER. The catalysts may be supported on resins, clays, zeolites and carbons. One example of a support is a chelating resin which contains an amino-carboxylic acid functional group. The chelating resin may be in the acid form or the salt form (FIG. 11). The acid form of the chelating resin is preferred. Chelating resins are commercially available, e.g., Dianon CR-11 from Mitsubishi Chemicals, Lewatit TP-208 from Bayer Chemicals and Amberlite IRC-748 from Rohm & Haas. A mixture of the acid form and the salt form of the chelating resin may be formed in a salt:acid molar ratio from 2:1 to 1:2, preferably 1:1 to 1:2, more preferably about 1:2.

In a process for preparing an alkylene glycol by reacting alkylene oxide with water in the presence of a catalyst of the present invention, a mixture of alkylene oxide and water in the liquid state is contacted with an amphoteric catalyst. The process is carried out at a temperature from about 20° C. to 250° C., preferably 50° C. to 200° C. and a pressure greater than atmospheric, preferably 25 psig to 1000 psig with the temperature and pressure selected to maintain liquid phase conditions. The molar ratio of alkylene oxide to water is in the range from about 5 to 25.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1-13 AND COMPARATIVE EXAMPLE

All experiments were performed in a batch mode in a Multiclave™. The catalyst was loaded into each reactor tube of the Multiclave™, 5 ml of water added to dissolve or suspend the catalyst and 10 ml of 4:1 (weight ratio) water/EO was added at 100° C. into the individual tubes of the Multiclave™ using a stream selector valve, a pump and a timer. The reactor was blanketed with 250 psig of $N_2$ or $CO_2$ and the reaction mixture stirred overnight. Products were analyzed by GC using a FID detector. Selectivities to MEG, DEG and TEG are calculated using the number of moles of EO used to form the glycols divided by total moles of EO converted. Reactions were run at 100° C. for 10 hours to assure complete conversion of EO. Selectivities were compared to a control experiment (Comparative Example) using a tube filled with the same volume but with no catalyst present. The results are shown in Table 1.

Material were purchased as ACS grade or better from Sigma/Aldrich unless otherwise specified: Iminodiacetic acid disodium salt (Fluka>95%); PIPES, dipotassium salt (Fluka>99%); diammonium EDTA (Fluka>99%); disodium nitrilotriacetic acid (Strem); poly-D,L-aspartic acid (MW=3000, 40% aqueous); 3-pipiradino-1,2-propanediol (Alfa); D-L-picolinic acid )Acros). The chelating resins were obtained from the manufacturers in the commercial grade and converted to the desired acid form or salt form per the manufacturers recommendations (typically, treating with dilute inorganic acid or sodium hydroxide): Dianon CR-11 from Mitsubishi Chemicals, Lewatit TP-208 from Bayer Chemicals and IRC-748 from Rohm & Haas. The EDTA salts were all purchased except for the sodium EDTA, which was prepared in situ from EDTA and disodium EDTA as noted below.

TABLE 1

Selectivity to MEG using amphoteric catalysts

| Catalyst | Amount(g) | pH | MEG Sel |
|---|---|---|---|
| None (Control) | 0 | 6 | 83.7% |
| 3-Pipiradino-1,2-Propanediol, 96% | 0.34 | 9 | 90.7% |
| Iminodiacetic Acid disodium salt | 0.4 | 10 | 86.2% |
| 2-Picolinic acid, 99% | 2.6 | 9 | 82.4% |
| D,L-Pipecolinic Acid | 0.2 | 4 | 84.3% |
| Piperazine-1,4-bis (2-ethanesulfonic acid), 98.5% | 0.33 | 5 | 88.8% |
| Pipes dipotassium salt | 0.55 | 9 | 89.4% |
| $(NH_4)_2$EDTA | 0.2 | 6 | 92.7% |
| Nitrilotriacetic acid | 0.2 | 3 | 91.3% |
| Nitrilotriacetic acid disodium salt (0.2 M) | 0.2 | 8 | 92.5% |
| N-Lauroylsarcosine sodium salt (NLS) | 0.96 | 8 | 92.2% |
| Na-D,L-isoascorbate | 1.0 | 9 | 94.0% |
| Poly-D-L-aspartic acid (sodium salt) | 1.1 | 9 | 92.5% |

EXAMPLES 14-21 AND COMPARATIVE EXAMPLE 2

Approximately 1 mmol of EDTA or its derivatives (NaEDTA was made in situ from equal parts of EDTA and $Na_2$EDTA was loaded into each reactor tube of the Multiclave™, and 10 ml of 4:1 (weight ratio) water/EO was added at 100° C. The reactor was blanketed with 250 psig of $N_2$. The results are shown in Table 2.

TABLE 2

Selectivity to MEG using EDTA and its derivatives as catalysts

| Catalyst | pH value | MEG Selectivity |
|---|---|---|
| None (or Control) |  | 83.0% |
| EDTA | 2 | 86.1% |
| NaEDTA | 4 | 89.3% |
| $Na_2$EDTA | 7 | 85.6% |
| $Na_3$EDTA | 10 | 55.1% |
| $Na_4$EDTA | 11 | 55.1% |
| KEDTA | 4 | 83.6% |
| $K_2$EDTA | 6 | 90.8% |
| $K_3$EDTA | 11 | 53.2% |

It should be noted that while the MEG selectivities for mono- and di-salts are the same or better than that for EDTA, the MEG selectivities for tri- and tetra-salts are less than that for EDTA.

EXAMPLES 22-46 AND COMPARATIVE EXAMPLE 3

Approximately 5 mL of a chelating resin (Dianon CR-11 from Mitsubishi Chemicals, Lewatit TP-208 from Bayer Chemicals and Amberlite IRC-748 from Rohm & Haas, as specified) or a mixture of the salt form and the acid form of a chelating resin was loaded into each reactor tube of the Multiclave™, and 10 ml of 4:1 (weight ratio) water/EO was added at 100° C. The reactor was blanketed with 250 psig of $N_2$. The results are shown in Table 3

TABLE 3

Selectivity to MEG using chelating resins

| Catalyst | pH | MEG Selectivity |
|---|---|---|
| None (or control) | 6 | 83% |
| CR11: $Na+_2$ | 12 | 68% |
| CR11: $Na+_2$:$H+_2$ = 2:1 (molar) | 8 | 80% |
| CR11: $Na+_2$:$H+_2$ = 1:1 (molar) | 7 | 86% |
| CR11: $Na+_2$:$H+_2$ = 1:2 (molar) | 7 | 89% |
| CR11: $H+_2$ | 5 | 87% |
| TP208: $Na+_2$ | 6 | 73% |
| TP208: $Na+_2$:$H+_2$ = 2:1 (molar) | 11 | 83% |
| TP208: $Na+_2$:$H+_2$ = 1:1 (molar) | 7 | 86% |
| TP208: $Na+_2$:$H+_2$ = 1:2 (molar) | 6 | 88% |
| TP208: $H+_2$ | 4 | 87% |
| IRC748: $Na+_2$ | 6 | 68% |
| IRC748: $Na+_2$:$H+_2$ = 2:1 (molar) | 10 | 80% |
| IRC748: $Na+_2$:$H+_2$ = 1:1 (molar) | 7 | 84% |
| IRC748: $Na+_2$:$H+_2$ = 1:2 (molar) | 6 | 89% |
| IRC748: $H+_2$ | 5 | 83% |

It should be noted that the acid form of chelating resin has higher MEG selectivity than the salt form. While a molar mixture of the salt and acid forms of chelating resin would be expected to have a selectivity between the selectivity for the salt form alone and the selectivity for the acid form alone, the salt to acid mixtures of 1:1 and 1:2 have selectivities which are about the same or better than the selectivity for the acid form alone.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for the preparation of alkylene glycols comprising reacting an alkylene oxide with water in the presence of an amphoteric compounds having both acid and base moieties, the base moiety is an amine, amide, imide, phosphazene, verkade base, nucleic acid or aminophospholipid group and the acid moiety is carboxylic, sulfonic, phosphoric, boric, nitric or salts thereof,
    wherein the process is carried out at a temperature from about 20° C. to 250° C. and at a pressure greater than atmospheric with the temperature and pressure selected to maintain liquid phase conditions.

2. A process as in claim 1 wherein the acid moiety contains a modifying group selected from the group of nitro, fluorinated alkyl and fluorinated aryl.

3. A process as in claim 1 wherein the amphoteric compound forms a buffered solution in water.

4. The process as in claim 3 wherein the buffered solution has a pH between 2-10.

5. The process as in claim 4 wherein the pH is between 5-10.

6. The process as in claim 5 wherein the pH is between 4-9.

7. The process as in claim 1 wherein the amphoteric compound is organic with the base moiety and the acid moiety being separated by one to four carbon atoms.

8. The process as in claim 1 wherein the organic compound is alkyl or aryl or combinations thereof.

9. The process as in claim 1 wherein the amphoteric compound is (ethylenedinitrilo) tetraacetic acid (EDTA), 3-piperadino-1,2-propanediol, N-(2-acetamido)imiodiacetic acid monosodium salt, 2-picolinic acid, DL-picolinic acid, piperazine- 1,4-bis-(2-ethanesulfonic acid), nitrilotriacetic acid, piperazine- 1,4-bis(2-ethanesulfonic acid).

10. The process as in claim 1 wherein the amphoteric compound is a Group 1-12 metal salt derivative.

11. The process as in claim 10 wherein the amphoteric compound is a Group 1 metal salt derivative having the formula $X_x$EDTA where X is a Group 1 metal and x is 1 to 4.

12. The process as in claim 1 wherein X is sodium or potassium.

13. The process as in claim 1 wherein x is 1 to 3.

14. The process as in claim 1 wherein x is 1 or 2.

15. The process as in claim 1 wherein the amphoteric compound is imiodiacetic acid disodium salt, piperazine-1,4-bis(2-ethanesulfonic acid) dipotassium salt, disodium nitrilotriacetic acid, poly-D-L-aspartic acid (sodium salt).

16. The process as in claim 1 wherein the amphoteric compound is heterogenized and supported on resins.

17. The process as in claim 1 wherein the amphoteric compound is a chelating resin which contains an aminocarboxylic acid functional group.

18. The process as in claim 16 wherein the chelating resin is the acid form.

19. The process as in claim 16 wherein the chelating resin is a mixture of the acid form and the salt form in a salt:acid molar ratio from 2:1 to 1:2.

20. The process as in claim 19 wherein the molar ratio is 1:1 to 1:2.

21. The process as in claim 20 wherein the molar ratio is about 1:2.

22. The process as in claim 1 wherein the temperature is 50° C. to 200° C.

23. The process as in claim 1 wherein the pressure is 25 psig to 1000 psig.

24. The process as in claim 1 wherein the process is carried out at a molar ratio of alkylene oxide to water in the range from about 5 to 25.

25. The process as in claim 1 wherein the alkylene oxide is reacted with water in the presence of carbon dioxide.

* * * * *